United States Patent [19]

Imai

[11] Patent Number: 5,641,646
[45] Date of Patent: Jun. 24, 1997

[54] PROCESS FOR PREPARATION OF HUMAN GLICENTIN

[75] Inventor: Shinjirou Imai, Ohimachi, Japan

[73] Assignee: Nisshin Flour Milling Co., Ltd., Tokyo, Japan

[21] Appl. No.: 365,109

[22] Filed: Dec. 28, 1994

[30] Foreign Application Priority Data

Dec. 28, 1993 [JP] Japan ..................... 5-349030

[51] Int. Cl.[6] .............. C12P 21/06; C12P 21/02; C07K 14/605
[52] U.S. Cl. ................ 435/68.1; 435/69.7; 530/308
[58] Field of Search ................. 435/69.7, 68.1; 530/308

[56] References Cited

U.S. PATENT DOCUMENTS

| | | | |
|---|---|---|---|
| 5,126,249 | 6/1992 | Becker et al. | 435/68.1 |
| 5,310,876 | 5/1994 | Bayer et al. | 530/350 |
| 5,432,156 | 7/1995 | Matsuno et al. | |

FOREIGN PATENT DOCUMENTS

| | | |
|---|---|---|
| 0 586 812 A2 | 3/1994 | European Pat. Off. |
| 4-364199 | 12/1992 | Japan. |
| 5-160977 | 6/1993 | Japan. |

OTHER PUBLICATIONS

Ford, C.F. et al. (1991) "Fusion tails for the recovery and purification of recombinant proteins" *Protein Expr. Purif.* 2(2–3):95–107.

Persson, M. et al. (1988) "Enzyme purification by genetically attached polycrysteine and polyphenylalanie affinity tails" *Anal. Biochem.* 172(2):330–337.

Iwakura M. et al. (1993) "immobilization of dihydrofolate reductase by engineered cysteine residue attached to its C-terminal end" *J. Biochem.* 114(3):339–343.

"The Enzymes" edited by Paul D. Boyer, pp. 105–111, vol. III, IV Dipeptidyltransferase, Academic Press, NY, 1971.

F.W. Studier et al., Methods in Enzymology, vol. 185, pp. 60–89 (1990).

"Proceedings of the Thirteenth Gut Hormone Conference", edited by Japanese Society of Gut Hormones, 1992, vol. 11, pp. 394–401.

Peptide Chemistry 1992, pp. 158–161, 1993, Tohru Mochizuki, et al., "Total Synthesis of Human Glicentin".

*Primary Examiner*—Robert A. Wax
*Assistant Examiner*—Kawa Lau
*Attorney, Agent, or Firm*—Oblon, Spivak, McClelland, Maier & Neustadt, P.C.

[57] ABSTRACT

Disclosed is a process for the preparation of native human glicentin, which comprises producing by gene technology a fused protein composed of human glicentin having a peptide moiety connected to the N-terminus of human glicentin and removing the connected peptide moiety from the fused protein, the improvement in which a purification of the fused protein and human glicentin is carried out by utilizing a reversible covalent bond of a cystein residue with the stationary phase of a chromatography.

4 Claims, 9 Drawing Sheets

PROCESS FOR PREPARATION OF HUMAN GLICENTIN

FIELD OF THE INVENTION

This invention relates to an improved process for the preparation of native human glicentin, which comprises producing a fused protein connected with a peptide to the N-terminus of human glicentin by gene technology, followed by removal of a connected peptide moiety, to achieve easy removal of the peptide moiety and the contaminants produced during the process.

BACKGROUND OF THE INVENTION

Glicentin is a gastrointestinal peptide hormone composed of 69 amino acids which plays an important role in the physiology of gastrointestines and is used in pharmaceuticals, e.g., antidiabetics as disclosed in EPA 0586812.

For commercial production of a useful protein such as human glicentin, a process has been extensively used, which includes producing a fused protein by gene technology by connecting the desired useful protein with a second peptide or a protein and purifying the resultant second protein followed by removing the second peptide or protein portion. Such a process to express a fused protein is expected to increase a production because of an increased expression, an easier purification, an increased stability in production process and an increased secretory efficiency in comparison with a direct expression of the desired useful protein.

However, it is necessary, when a useful protein prepared by gene technology is used as drugs, foods or the like, to remove methionine at the amino terminus encoded by the translation initiation codon attached to a useful protein, since methionine may bring about an immunogenicity. In case of the production by a direct expression of a useful protein, methionine at the amino terminus sometimes remains unremoved, and therefore a process is often used for practical production of a useful protein to produce a fused protein and to remove methionine by digesting the unnecessary moiety.

In producing a useful protein by this process, however, there is a possibility that a part of the fused protein is degraded. This degradation produces contaminants as by-products which are difficult to remove from the desired product. These occurrences lead to a possible contamination of the fused protein or undegraded contaminants in the desired product, and these inclusions are difficult to be removed since the characters of these inclusions are similar to the desired product. Furthermore, these inclusions may possibly bring about an antigenicity like an additional methionine at the amino terminus when the desired product is used as drugs, foods or the like, and therefore it has been highly required to develop an effective removal method of the amino terminal methionine and these contaminants.

In a commercial production of a human glicentin by such processes as disclosed in Japanese Patent Kokai 4-364199 and Japanese Patent Application Hei 5-160977, the presence of a trace amount of contaminants is anticipated, thus requiring a further purification for use as a drug.

Furthermore, a production of proteins in *Escherichia coli* by gene technology often digests a part of proteins in *E. coli* with the protease of *E. coli* itself and results in an inclusion of digested contaminants in the product. It is necessary to remove contaminants as well as the digested substance in a purification process of the afore-mentioned fused proteins or contaminants produced in a cleavage process of the desired protein from a fused protein. In this case, however, it is difficult to remove contaminants since it resembles the desired protein.

Human glicentin is currently produced as a fused protein and also contains contamination from the cleavage reaction. It is highly desirable to find a purification process suitable for removing these contaminants.

On one hand, an effort to purify the desired peptide by introducing a cysteine residue into a peptide has been carried out in the chemical synthesis of peptides. The process is to add the cysteine-methionine sequence to the amino terminus of the desired peptide and to remove, via affinity chromatography against the added cysteine residue, the peptides of which synthesis was terminated before reaching the desired peptide. Even if this method is applied to the synthesis of human glicentin, pure human glicentin cannot be achieved since methionine remains in human glicentin and such human glicentin is decomposed by cyanogen bromide mediated cleavage. The production of long-chain peptides at an industrial level by this chemical synthesis method is practically impossible due to the cost.

SUMMARY OF THE INVENTION

An object of the present invention is, in the preparation of human glicentin by gene recombination technology, to produce a fused protein connected with the peptide containing a specific amino acid residue at the amino terminus of human glicentin, providing easy purification of the fused protein. A further object of the invention is to provide an easy method for the isolation and removal of an undigested fused protein in a purification of human glicentin after digesting the connected peptide moiety from the fused protein with cathepsin C.

According to the invention, there is provided a process for the preparation of native human glicentin, which comprises producing by gene technology a fused protein composed of human glicentin having a second peptide moiety connected to the N-terminus of human glicentin and removing the connected second peptide moiety from the fused protein, the improvement in which a purification of the fused protein and human glicentin is carried out by forming a reversible covalent bond between a cysteine residue in the second protein and a thiol group in the stationary phase of a chromatography column or with a thiol-containing reagent.

BRIEF DESCRIPTION OF DRAWINGS

FIG. 6 is a photograph showing an electrophoresis pattern of the sample containing the fused protein of human glicentin and the like.

DETAILED DESCRIPTION OF THE INVENTION

Figure 1:
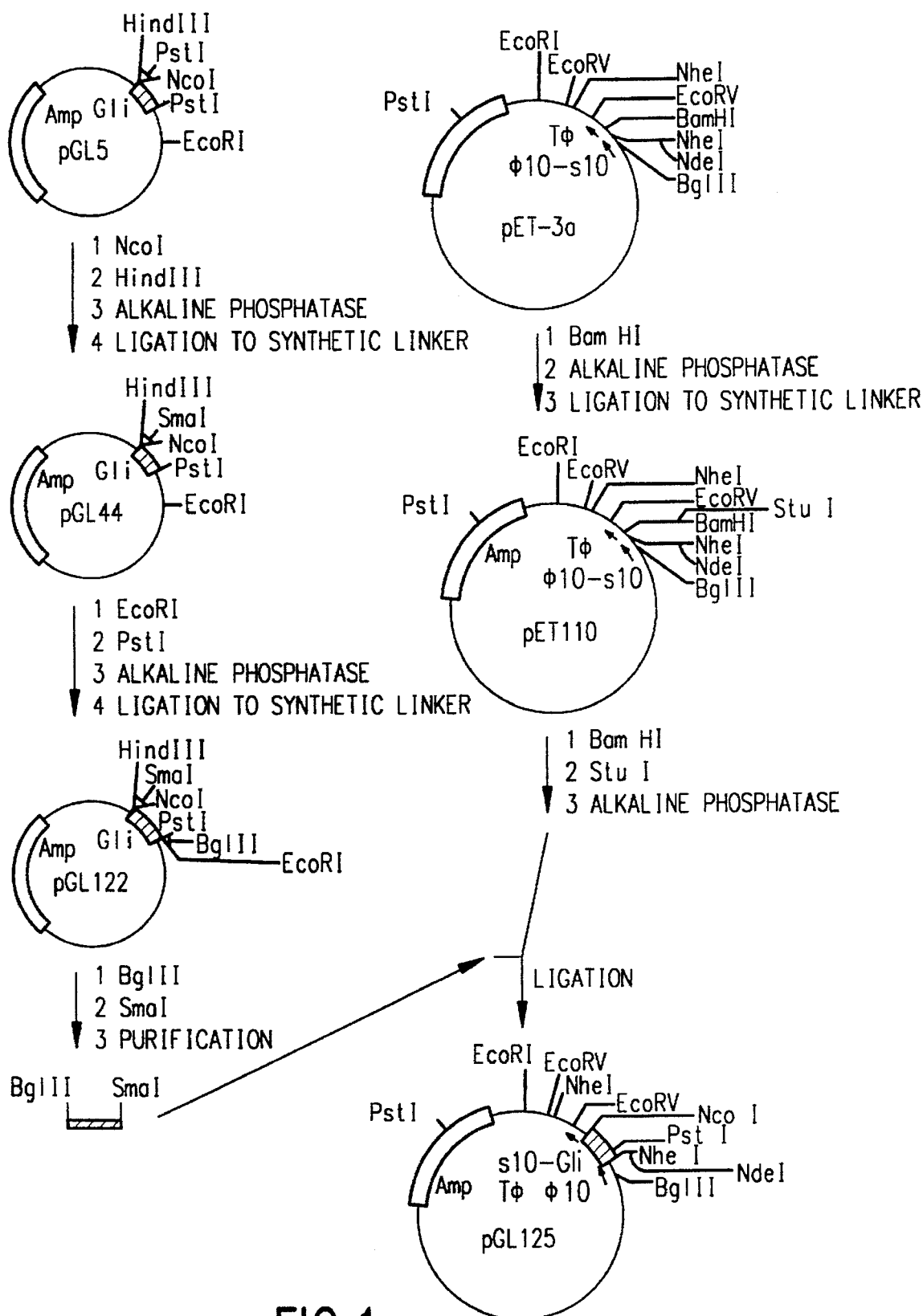
FIG. 1 is a flow diagram illustrating the process steps for the construction of plasmid pGL125.

In producing human glicentin by gene technology, cysteine is introduced into the peptide portion to be added. In this manner, a fused protein is purified from the extracts which include the host-derived impurities and contaminants of the fused proteins. Subsequently, the added peptide moieties of the fused protein are digested with cathepsin C. The added peptide moiety of a fused protein contains a cysteine residue, but the desired human glicentin does not contain it. An isolation and removal of contaminants from human glicentin to be selected by whether or not a cysteine residue is present can be easily achieved by the purification method utilizing the characteristics of the cysteine residue.

The characteristic of the cysteine residue is to form a disulfide bond by oxidation of a thiol radical and again cleave the disulfide bond easily under reduction condition. Such a character as capable of forming a reversible covalent bond is unique to cysteine, and not found in any other amino acids constituting proteins. Relying on such unique character of cysteine, a covalent chromatography using as a stationary phase, e.g., 2-pyridyl disulfide hydroxypropylether sepharose such as thiopropylsepharose 6B (trade name by Pharmacia Biotech) can be employed to achieve a selective adsorption of proteins onto the stationary phase followed by elution.

Other purification method utililizing this character includes a process of introducing a thiol reactive reagent such as 2,2'-dipyridilsulfide, Ellman's reagent and the like into a cysteine residue to alter the characteristic of fused protein and purifying by a conventional chromatography. Those thiol reagents lead to a hydrophobic increase of the fused protein transduced and an increase of separation efficiency by a chromatography. In case an extreme alteration of the character of a fused protein is desired, a thiol reactive reagent may employ the substance wherein a heterobifunctional reagent, SPDP (N-succinyimidil-3-(2-pyridylthio)propionate) is reacted with any protein, an amino group-containing chemical substance. For example, if SPDP is transduced into a protein A which is a specific binding substance for immunoglobulin and then connected with a cysteine residue in the desired fused protein, an affinity chromatography can be achieved by an immunoglobulin fixed column, by which a fused protein having a cysteine residue can be isolated.

In this invention, the connected peptide moiety in the fused protein contains arginine and/or lysine in addition to cysteine. One of the purposes to introduce arginine and/or lysine is to achieve easy removal of contaminants incorporated during the course of purification steps of a fused protein. This is based on the findinga that an isoelectric point of a fused protein becomes higher than that of human glicentin due to the introduced arginine and/or lysine, while an isoelectric point of contaminants is lower than that of human glicentin or equal, which results in removal of contaminants by such means as ion exchange chromatography.

Another purpose to introduce arginine and/or lysine is based on the following finding. In the production of a fused protein in E. coli, if methionine as a translation initiating amino acid is not completely removed in the bacteria or if there is present the degraded substance in which odd-numbered amino acids are lacking from the amino-terminal alanine of a fused protein, a cleavage of these contaminants is terminated just before the introduced arginine by a digestion with cathepsin C, which results in no contamination of a degraded substance of smaller molecule than glicentin which was present as a mixture when arginine and/or lysine was not introduced. Since the impurities upon which digestion was terminated just before the introduced arginine and/or lysine contain cysteine, those impurities can be removed by a purification process utilizing the characteristics of cysteine.

In order to establish the above-mentioned findings, the positions of arginine and/or lysine are designed to be located at the even-numbered positions from the amino terminus of a connecting peptide moiety. This is to design a digestion of the connecting peptide moiety terminated at the 1st positioned arginine of human glicentin, not terminated at the positions of the introduced arginine or lysine, when digested with cathepsin C. The above methodology utilizes the specificity of cathepsin C cathepsin C digests each 2 amino acids from the amino terminus of a protein substrate and stops digesting when arginine or lysine appears at the amino terminus ("The Enzymes" edited by Paul D. Boyer, pp. 105–111, Vol. III, IV Dipeptidyltransferase, Academic Press, NY, 1971). The digestion does not stop when arginine or lysine appears at the 2nd position from the amtno terminus.

It is preferable to introduce cysteine at the 1st and/or 2nd positions to the amino-terminal direction of a fused protein from the amino-terminal arginine of human glicentin for the purpose of cysteine being contained in a minimum unit of incompletely digested substance which may be formed in the isolation of human glicentin from the fused protein with cathepsin C.

It is basically preferable to introduce arginine or lysine at the 1st position to the amino-terminal direction of the fused protein from N-terminal arginine of a human glicentin with a view to have the cysteine residue included in the impurities present after a treatment with cathepsin C when there are mingled the molecules lacking in odd-numbers at the N-terminus of the fused protein or the molecules in which methionine as a translation initiation amino acid remains unremoved.

In this invention, however, it was found most preferable to introduce arginine or lysine at the 5th position of N-terminus of a fused protein from the N-terminus of a human glicentin, since a reactivity of cysteine is enhanced, compared with a case that cysteine was designed to locate at the 1st position to the amino-terminal direction of a fused protein from the N-terminal arginine of a human glicentin. This reason is that, when basic amino acids such as arginine or lysine are positioned before or after a cysteine residue, pKa of cysteine decreases, leading to a decreased reactivity of cysteine.

This invention enables one to remove with only two purification steps non-specific degraded materials which have not been removed by a conventional method using an affinity chromatography or required a great efforts for achievement. Furthermore, the invention provides means for achieving easy purification to remove undigested substances mingled upon cleavage of the desired protein from the fused protein by gene technology.

The invention is further illustrated by the following examples, in which there are used M9ZB culture medium, GAE buffer, AES buffer and TES buffer having the following composition. M9ZB culture medium: per liter NZ amine 10 g, NaCl 5 g, $NH_4Cl$ 1 g, $KH_2PO_4$ 3 g, $Na_2HP_4$ 6 g, glucose 4 g, $MgSO_4 \cdot 7H_2O$ 264 mg, ampicillin 50 mg GAE buffer:

4M guanidine chloride, 0.1M sodium acetate, pH 4.5, 1 mM EDTA

AES buffer:

0.1M sodium acetate, pH 4.5, 1 mM EDTA, 0.5M NaCl

TES buffer:

0.1M Tris HCl, pH 7.5, 1 mM EDTA, 0.5M NaCl

EXAMPLE 1

Construction of Expression Vector Plasmid pGL147

An expression vector was constructed in which a fused glicentin gene was linked downstream of T7φ10 promoter. A series of experimental operations was carried out in accordance with conventional experimental methods for gene technology.

In order to carry out the linkage of the glicentin gene DNA, an Stu I recognition sequence was inserted into vector plasmid pET-3a (available from Novagen, U.S.A.) downstream of the Bam HI recognition sequence.

Two oligonucleotides of the following sequences:

5'-GATCCTTAGCGTAGGCCTT-3' (SEQ ID NO: 1 in the Sequence Listing), and

5'-GATCAAGGCCTACGCTAAG-3' (SEQ ID NO: 2 in the Sequence Listing)

were synthesized, using a Cyclone Plus DNA synthesizer manufactured by Milligen/Biosearch and synthetic reagents also supplied by the same manufacturer, in accordance with the accompanying operation manual. These oligonucleotides were purified by use of an Oligo-Pak™ manufactured by Milligen/Biosearch and the accompanying oligonucleotide purification manual. These procedures were used to perform the synthesis and purification of all the oligonucleotides to be used in the experiments which follow. Five μg of each oligonucleotide was phosphorylated with T4 polynucleotide kinase manufactured by Takara Shuzo under the reaction conditions as commended by the manufacturer. The two reaction solutions were combined together, incubated at 90° C. for 5 minutes and then cooled down to 30° C. over a period of 3 hours to carry out the annealing of oligonucleotides. Plasmid pET-3a (see, F. W. Studlet et al., Methods in Enzymology, Vol. 185, pp. 60–89 (1990)) was hydrolyzed with Bam HI and then dephosphorylated with E. coli alkaline phosphatase manufactured by Takara Shuzo under the reaction conditions as commended by the manufacturer. The resultant linear plasmid and the annealed oligonucleotides were ligated together using a DNA ligation kit manufactured by Takara Shuzo in accordance with the protocol as commended by the manufacturer. The ligated DNA Was used to transform E. coli JM109 using the calcium chloride technique and those transformants were selected which grew on LB agar culture media containing ampicillin at a concentration of 50 μg/ml. The resultant transformant was cultivated overnight in an LB medium containing ampicillin at a concentration of 50 μg/ml, followed by extraction and purification of plasmids from the bacterial culture. The resultant plasmids were subjected to hydrolysis with Stu I followed by agarose gel electrophoresis to select those plasmids which possess a cleavage site with this enzyme. The nucleotide sequence of these plasmids was determined by the dideoxy method using a Sequence version 2.0 kit manufactured by United States Biochemical Corporation in accordance with the protocol as commended by the manufacturer. The newly obtained plasmid was designated pET110. The pET110 was confirmed to have newly an Stu I recognition sequence downstream of the Bam HI recognition sequence. The nucleotide sequence between the Bam HI and Stu I recognition sequences is as follows:

5'-GGATCCTTAG CGTAGGCCT-3' (SEQ ID NO: 3 in the Sequence Listing)

The Pst I recognition sequence present downstream of the glicentin gene in pGL5 (see "Proceedings of the Thirteenth Gut Hormone Conference", edited by JAPANESE SOCIETY OF GUT HORMONES, 1992, Vol. 11, PP. 394–401) was converted into an Sma I recognition sequence.

Two oligonucleotides of the following sequences:

5'-CATGGCCCGGGACAGCACA-3' (SEQ ID NO: 4 in the Sequence Listing) and

5'-AGCTTGTGCTGTCCCGGGC-3' (SEQ ID NO: 5 in the Sequence Listing)

were synthesized and then subjected to purification, phosporylation and annealing in the same manner as described above. pGL5 was cleaved with Nco I and Hind III and the reaction products were subjected to agarose gel electrophoresis. The desired fragments were purified by extraction from the gel of the ca. 4 kb band. The thus purified linear plasmid was ligated with the annealed oligonucleotides. The ligated DNA was used to transform E. coli JM109 in the same manner as in the construction of the pET110. Again in the same manner as with the pET110 plasmids were extracted and purified from the transformant. The nucleotide sequence of the resultant plasmids were hydrolyzed with Sma I to select those plasmids in which a cleavage site with this enzyme was present. The nucleotide sequence of these plasmids was determined to select a plasmid having the desired sequence, which was designated pGL44. In the newly obtained plasmid pGL44, the Pst I recognition sequence downstream of a glicentin gene had been deleted and an Sma I recognition site added newly. The nucleotide sequence of the Nco I—Hind III region of the pGL44 including the new Sma I site placed downstream of the human glicentin gene is as follows:

5'-CCATGGCCCG GGACAGCAAG CTT-3' (SEQ ID NO: 6 in the Sequence Listing)

The 5'-terminal region of the human glicentin gene of pGL44 was substituted.

Two oligonucleotides of the following sequences:

5'-AATTCAGATCTATCGAAGGTCGACGTTCTCTG-CA-3' (SEQ ID NO: 7 in the Sequence Listing) and 5'-GAGAACGTCGACCTTCGATAGACTG-3' (SEQ ID NO: 8 in the Sequence Listing) were synthesized and then subjected to purification, phosphorylation and annealing in the same manner as described above. pGL44 was hydrolyzed with Eco RI and Pst I, dephosphorylated in the same manner as described above, and then ligated with the annealed oligonucleotides. The annealed DNA was used to transform E. coli JM109. Plasmids were extracted from the transformant and treated with Bgl II to select those plasmids which can be cleaved with this enzyme. The nucleotide sequence of these plasmids was identified and a plasmid having the desired nucleotide sequence was designated pGL122. The pGL122 was confirmed to have the synthetic oligonucleotides inserted into the Eco RI—Pst I site. The nucleotide sequence of the substituted site in the pGL122 is shown below:

5'-GAATTCAGAT CTATCGAAGG TCGACGTTCT CTGCAG-3' (SEQ ID NO: 9 in the Sequence Listing)

pGL122 was hydrolyzed with Bgl II and Sma I and the DNA fragment containing glicentin gene was purified. pET110 was hydrolyzed with Bam HI and Stu I and then dephosphorylated. The product was mixed with the DNA fragment containing glicentin gene and ligated thereto by using T4 DNA ligase. The reaction product was mixed with E. coli JM109 for transformation to obtain a new plasmid pGL125. The pGL125 is an expression vector in which downstream of the T7φ10 promoter is joined by the T7s10 peptide, an inserted amino acid sequence and a fused peptide gene of human glicentin. The process steps for the construction of pGL125 are schematically shown in FIG. 1. Construction of pGL144 pUC18 was cleaved with restriction enzyme Dra I and then subjected to agarose gel electrophoresis to purify the ampicillin-resistance gene-containing fragment. pGL125 was cleaved with restriction enzyme Dra I and then subjected to agarose gel electrophoresis to purify the ampicillin-resistance gene-free fragment. These fragments were subjected to ligation using T4 DNA ligase. The reaction product was introduced into competent E. coli JM109 cells and the transformant was selected on an ampicillin-containing selection medium.

Figure 2:
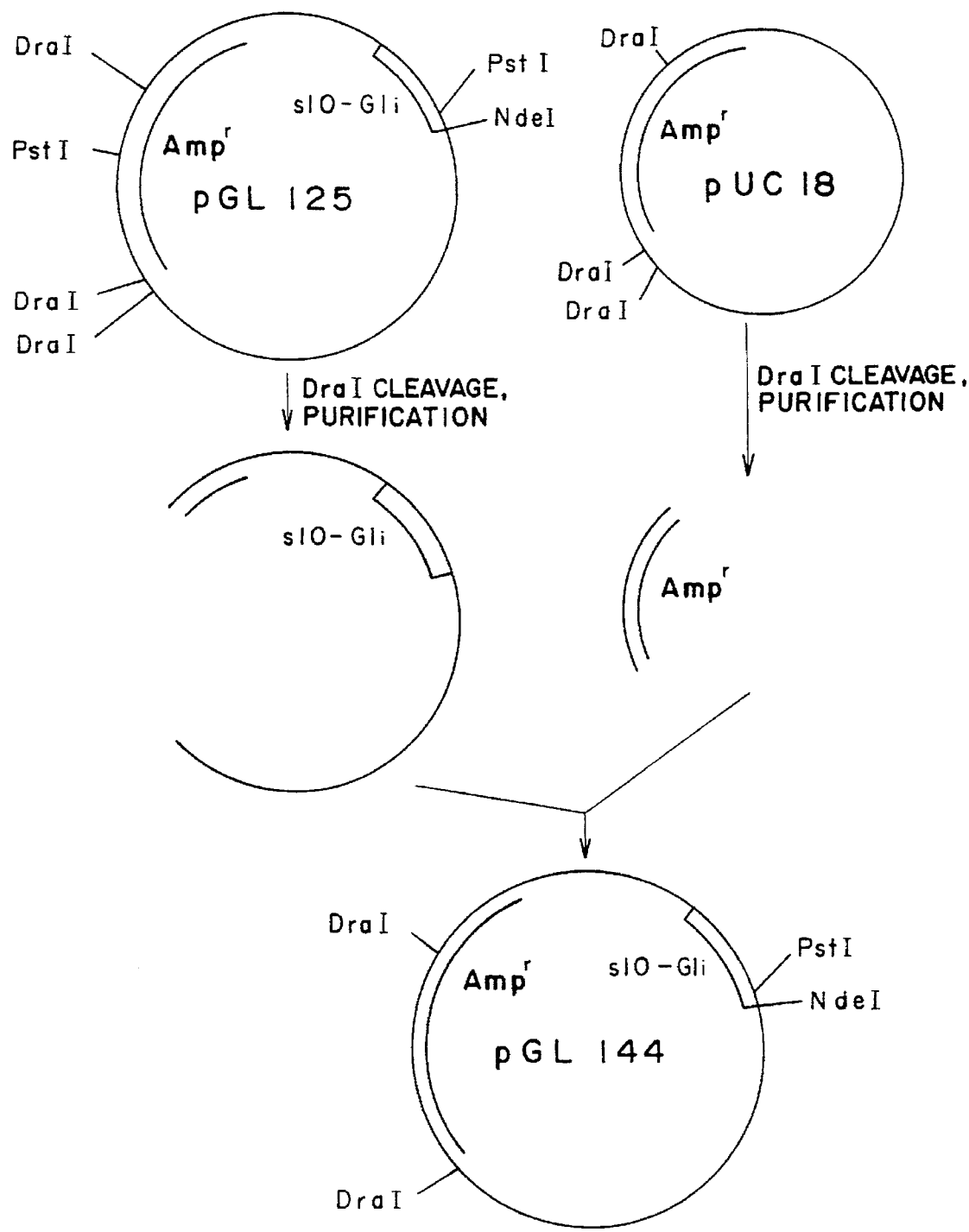
FIG. 2 is a flow diagram illustrating the process steps for the construction of plasmid pGL144.

Plasmid was extracted from the resultant transformant in accordance with a conventional method and a restriction enzyme cleavage map was prepared to confirm the construction of the desired plasmid, which was designated pGL144. The process steps for the construction of pGL144 are schematically shown in FIG. 2.

Thus constructed plasmid pGL144 containing the glicentin downstream of T7φ10 promoter was cleaved with restriction enzymes Nde I and Pst I, and a synthetic linker was inserted thereinto. The synthetic linker has the following DNA sequence:

5'-TATGGCTAGCATGACTGGTGGACAGCAAATGT-GTCGTTCCCTGCA-3' (SEQ ID NO: 10 in the Sequence Listing) and 5'-GGGAACGACACATTTGCTGTCCACCAGTCATG-CTAGCCA-3' (SEQ ID NO: 11 in the Sequence Listing)

Figure 3:
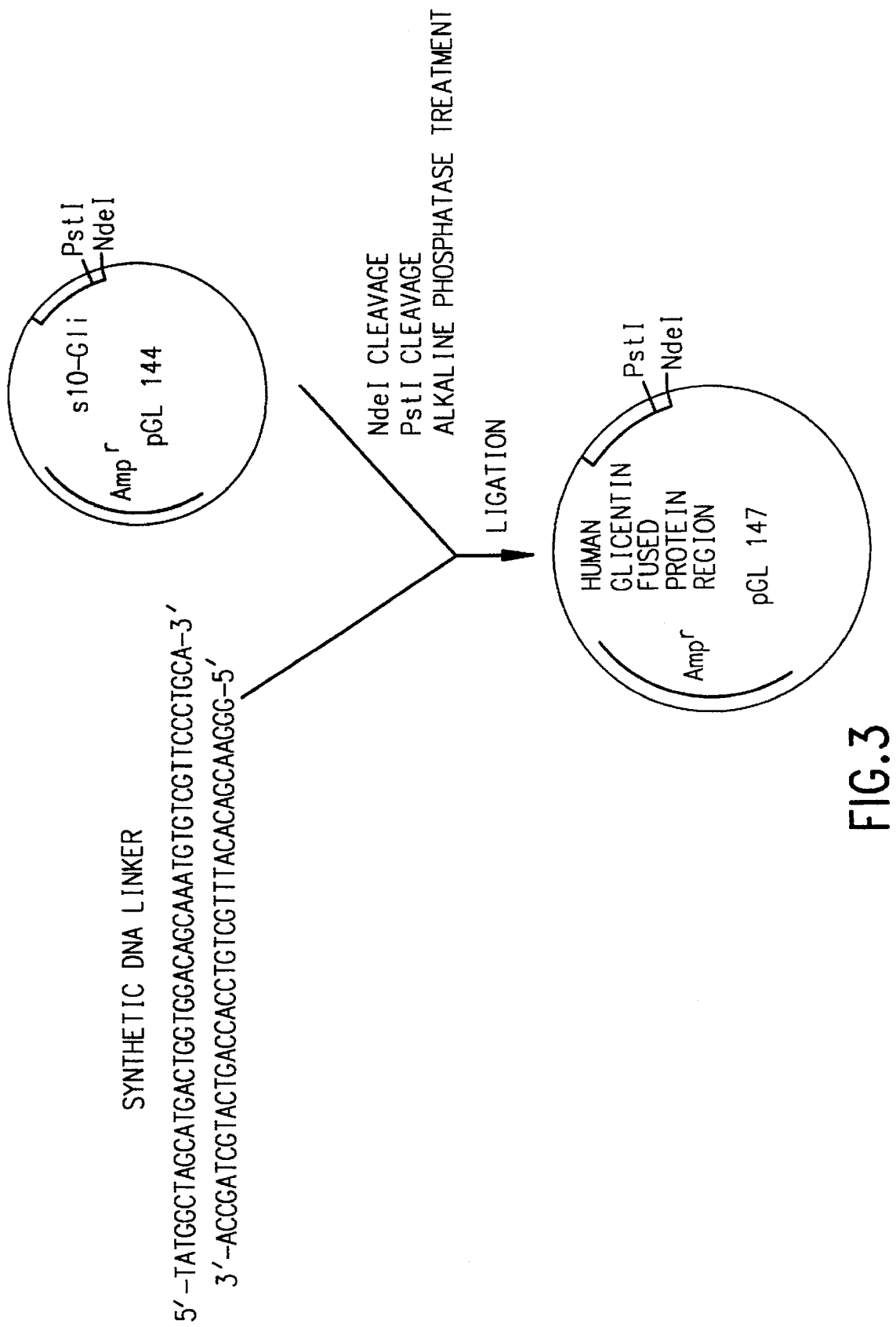
FIG. 3 is a flow diagram illustrating the process steps for the construction of plasmid pGL147 from the DNA of SEQ ID NO: 10.

Two μg each of the synthetic DNAs was separately phosphorylated with T4 polynucleotide kinase. The two reaction mixtures were combined and the resultant mixture was heated at 95° C. for 5 minutes and then cooled down to room temperature over a period of 1 hour for annealing. Using a DNA ligation kit manufactured by Takara Shuzo, the thus prepared synthetic DNA linker was ligated to a linear pGL144 obtained by cleavage with restriction enzymes Nde I and Pst I followed by purification by means of agarose gel electrophoresis. The thus ligated DNA was introduced into competent E. coli JM109 cells and the transformant selection was carried out on an ampicillin-containing selection medium. The plasmid was extracted from the resultant transformant in the conventional manner to confirm, using the dideoxy method by Sanger et al., that it had the desired base sequence. This plasmid was designated pGL147. The process steps for the construction of pGL147 are schematically shown in FIG. 3.

EXAMPLE 2

Construction of pGL149

The synthetic DNA linkers as shown below were connected with the linear pGL144 constructed in Example 1 which was cleaved with restriction enzymes Nde I and Pst I and purified.

5'-TATGGCTAGCATGACTGGTCGTCAGCAATGTG-GTCGTTCCCTGCA-3' (SEQ ID NO: 12 in the Sequence Listing) and 5'-GGGAACGACCACATTGCTGACGACCAGTCAT-GCTAGCCA-3' (SEQ ID NO: 13 in the Sequence Listing)

Figure 4:
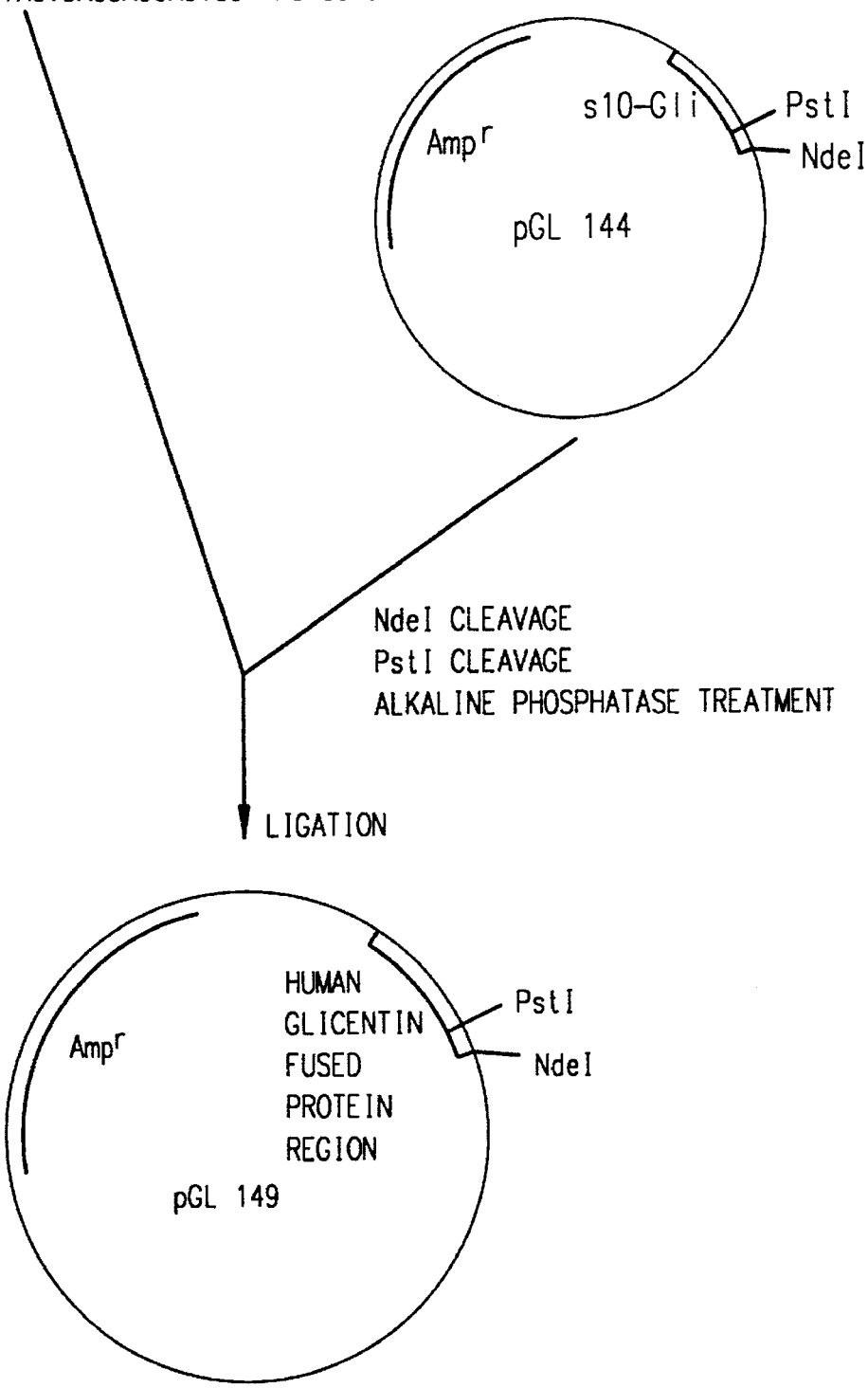
FIG. 4 is a flow diagram illustrating the process steps for the construction of plasmid pGL149 from the DNA of SEQ ID NO: 12.

Two μg each of the synthetic DNAs was separately phosphorylated with T4 polynucleotide kinase. Both reaction solutions were combined together and heated at 95° C. for 5 minutes and then cooled down to room temperature over a period of 1 hour for annealing. Using a DNA ligation kit manufactured by Takara Shuzo, the thus prepared synthetic DNA linker was ligated to the linear pGL144 obtained by cleavage with restriction enzymes Nde I and Pst I followed by purification by means of agarose gel electrophoresis. The thus ligated DNA was introduced into competent E. coli JM109 cells and the transformant selection was carried out on an ampicillin-containing selection medium. The plasmid was extracted from the resultant transformant in the conventional manner to confirm, using the dideoxy method by Sanger at al., that it had the desired sequence. This plasmid was designated pGL149. The process steps for the construction of pGL149 are shown in FIG. 4.

EXAMPLE 3

Production of a Human Glicentin Fused Protein E. coli HMS174(DE3) (available from Novagen, U.S.A.) was transformed separately with pGL147 shown in Example 1 and with pGL149 shown in Example 2 to give a transformant with the capability of producing a human glicentin fused protein. The transformant having pGL147 was designated G647, and the transformant having pGL149 was designated G662. These transformants were used to produce a human glicentin fused protein in the following manner.

Cultivation

The transformants G647 and G662 were respectively incubated in one liter of M9ZB culture medium at 37° C. IPTG (isopropylthiogalactoside) was added to a final concentration of 0.5 mM at a point when the absorbance $A_{550}$ reached 0.8 and then incubated for 2.5 hours to produce a human glicentin fused protein. The cultured bacteria of G647 and G662 was respectively 5 g by wet weight per liter of culture.

EXAMPLE 4

Figure 5:
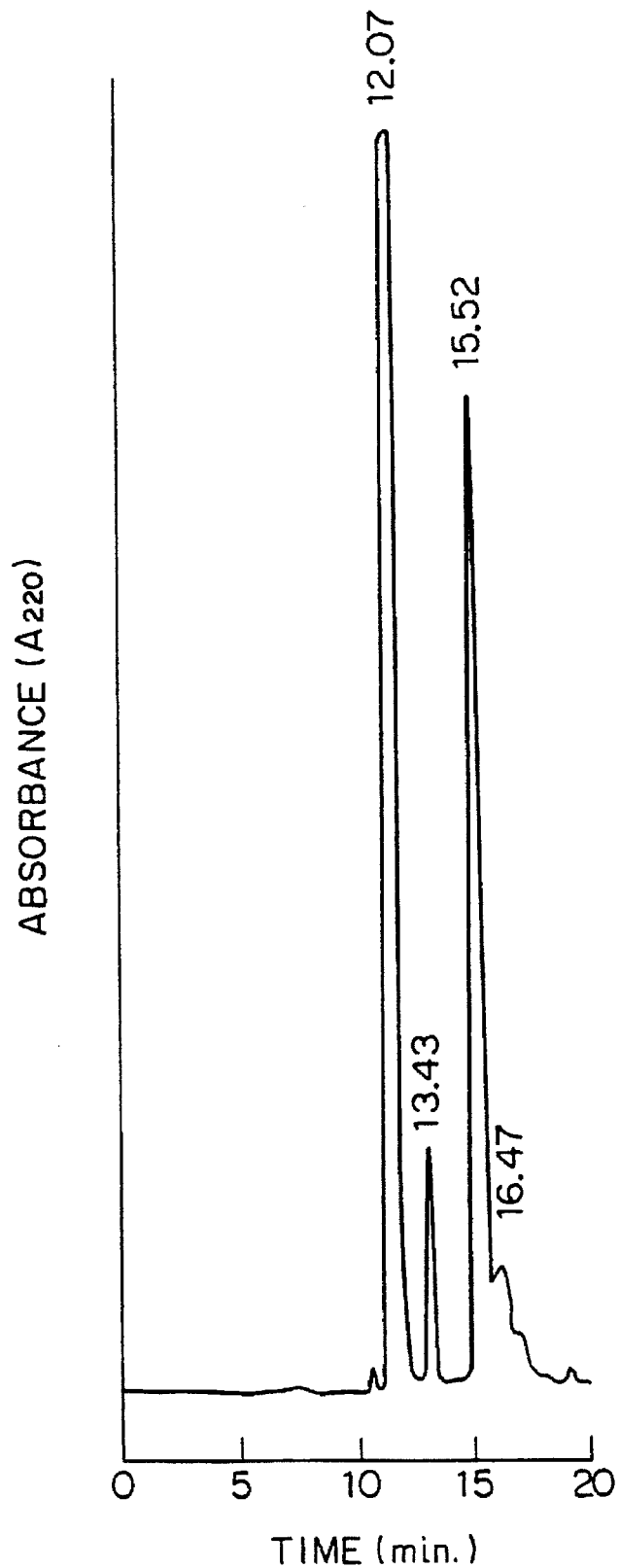
FIG. 5 is a HPLC chromatogram of a fused protein of human glicentin derived from G647.

Purification of a Fused Protein of G647-Derived Human Glicentin 5 g by wet weight of the G647 cultured bacteria was suspended in 30 ml of GAE buffer and sonificated. A supernatant was collected by centrifugation (25,000×G, for 10 minutes) and the supernatant was loaded on a thiopropylsepharose 6B column (1 cmφ×6.4 cm) which was previously washed with GAE buffer at a flow rate of 3 ml/hr. The column was washed successively with 100 ml of GAE buffer, 100 ml of AES buffer and 100 ml of TES buffer, and eluted with TES buffer containing 50 mM dithiothreitol at a flow rate of 10 ml/hr. To the eluted fractions was added 50% saturated ammonium sulfate to precipitate a human glicentin fused protein. The resultant precipitate was dissolved in 20 ml of 10 mM hydrochloric acid and then dialyzed against 20 mM sodium acetate buffer at pH 5.6. The solution was adsorbed on a cation exchanger CM52 column (1.6 cmφ×10 cm) manufactured by Wattman, which was previously washed with 20 mM sodium acetate buffer at pH 5.6, and the column was washed with 20 mM sodium acetate buffer at pH 5.6 and eluted in the same buffer containing 1M sodium chloride at a flow rate of 0.5 ml/min. with a linear gradient over a period of 100 minutes. The chromatogram of HPLC of the human glicentin fused protein is shown in FIG. 5. The peak appearing at 15.52 minutes in FIG. 5 identifies the human glicentin fused protein. The peak appearing at 12.07 minutes identifies β-mercaptoethanol added to the sample for inhibiting any non-specific adsorbance of the fused protein on the column. The conditions for HPLC were as follows:

Column: Inertsil ODS (10 mmφ×250 mm) manufactured by GL Science

Elution: Linear gradient over a period of 20 minutes from 20% acetonitril+10 mM hydrochloric acid to 40% acetonitril+10 mM hydrochloric acid Flow rate: 2 ml/min.

Detection: UV absorption at 220 nm

Figure 6:
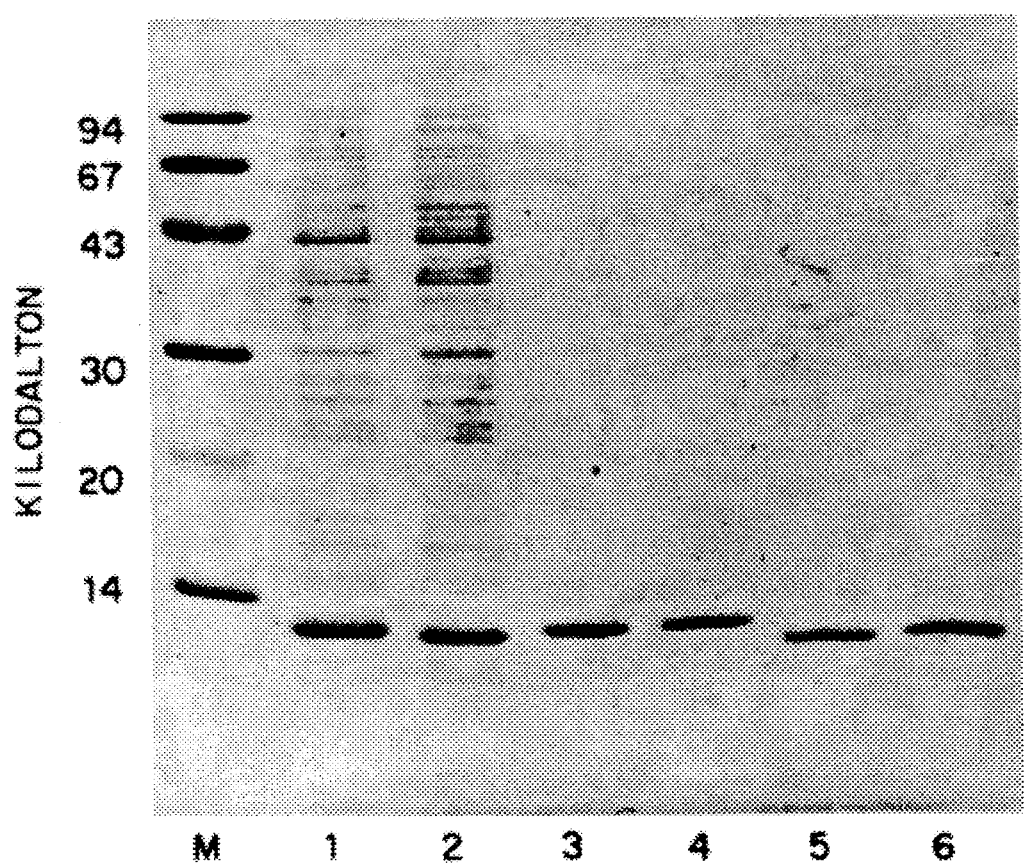

The analytical result of the pure preparation by SDS polyacrylamide gel electrophoresis is shown in FIG. 6. The lane 1 in FIG. 6 shows a load with an extract itself, and the lane 3 shows a load with a fused protein purified in the above manner.

By applying the pure preparation to a peptide sequencer, the first 13 amino-terminal amino acids were determined to have the sequence Ala-Ser-Met-Thr-Gly-Gly-Gln-Gln-Met-Cys-Arg-Ser-Leu-SEQ ID NO: 15 . . . Thus the preparation was found to be a human glicentin fused protein having the desired 10 amino acids connected to the amino terminus of native glicentin.

EXAMPLE 5

Figure 7:
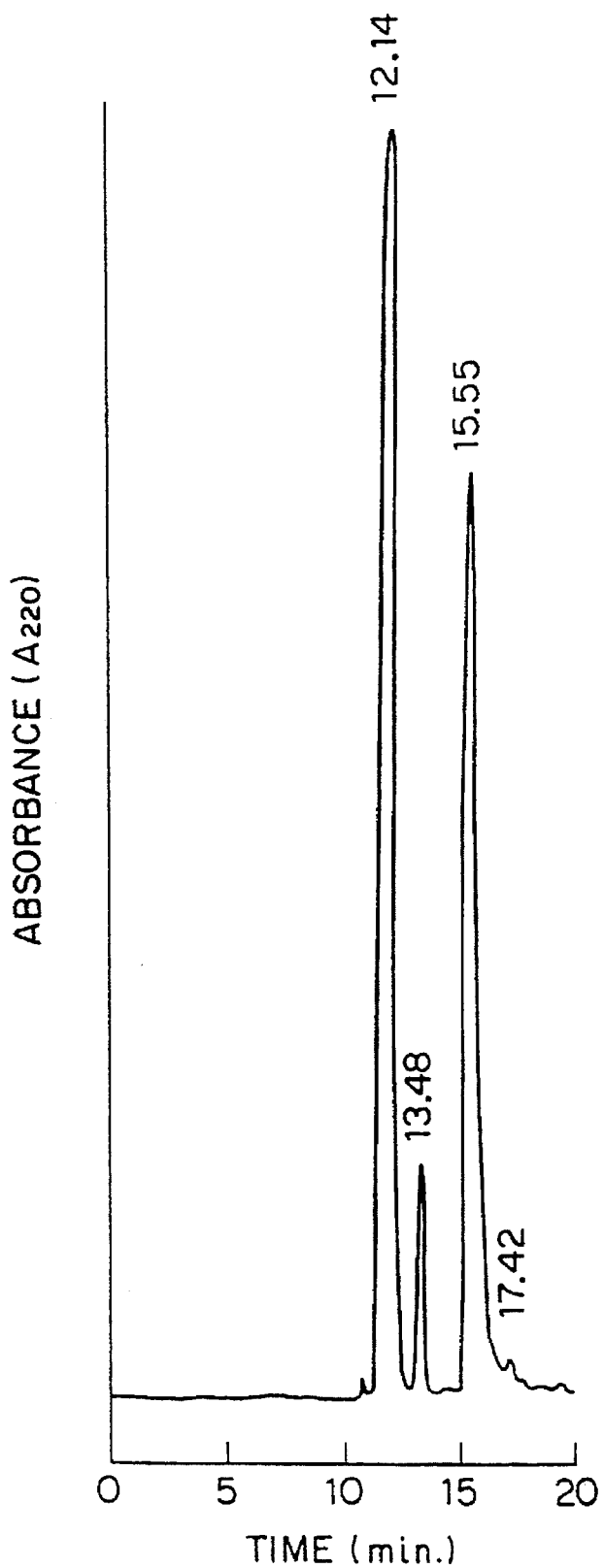
FIG. 7 is a HPLC chromatogram of the fused protein of human glicentin derived from G662.

Purification of a Fused Protein of G662-Derived Human Glicentin 5 g by wet weight of the G662 cultured bacteria was suspended in 30 ml of GAE buffer and sonificated. A supernatant was collected by centrifugation (25,000×G, for 10 minutes) and the supernatant was loaded on a thiopropylsepharose 6B column (1 cmφ×6.4 cm) which was previously washed with GAE buffer at a flow rate of 3 ml/hr. The column was washed successively with 100 ml of GAE buffer, 100 ml of AES buffer and 100 ml of TES buffer, and then eluted with TES buffer containing 50 mM dithiothreitol at a flow rate of 10 ml/hr. To the eluted fractions was added 50% saturated ammonium sulfate to precipitate a human glicentin fused protein. The resultant precipitate was dissolved in 20 ml of 10 mM hydrochloric acid and then dialyzed against 20 mM sodium acetate buffer at pH 6.5. The solution was adsorbed on a cation exchanger CM52 column (1.6 cmφ×10 cm) manufactured by Wattman, which was previously washed with 20 mM sodium acetate buffer at pH 6.5, and the column was washed with 20 mM sodium acetate buffer at pH 6.5 and eluted in the same buffer containing 1M sodium chloride at a flow rate of 0.5 ml/min. with a linear gradient over a period of 100 minutes. The HPLC chromatogram of a human glicentin fused protein is shown in FIG. 7. The peak appearing at 15.55 minutes in FIG. 7 identifies the human glicentin fused protein. The peak appearing at 12.14 minutes identifies β-mercaptoethanol added to the sample for inhibiting any non-specific adsorbance of the fused protein on the column. The conditions for HPLC were as shown in Example 4. The analytical result of the pure preparation by SDS polyacrylamide gel electrophoresis is shown in FIG. 6. The lane 2 in FIG. 6 shows a load with an effluent. The lane 4 represents a load with the fused protein purified as described above. As shown in FIG. 6, the fused protein was found to be substantially purified only with 2 steps.

The analytical result of the fused protein purified by the process illustrated in Example 4 are compared with those by the process illustrated in Example 5. No substantial change is found in both cases with respect to the results by SDS polyacrylamide gel electrophoresis. The peaks of impurities appearing after the peak of the human glicentin fused protein are not substantially found in those by the process illustrated in Example 5, but found in small number in those by the process illustrated in Example 4.

By applying the pure preparation to a peptide sequencer, the first 13 amino-terminal amino acids were determined to have the sequence Ala-Ser-Met-Thr-Gly-Arg-Gln-Gln-Cys-Gly-Arg-Ser-Leu-SEQ ID NO: 14 . . . Thus the preparation was found to be a human glicentin fused protein having the desired 10 amino acids connected to the amino terminus of native glicentin.

EXAMPLE 6

Removal of an Unnecessary Peptide Portion from a Human Glicentin Fused Protein

A human glicentin fused protein shown in Examples 4 and 5 was digested enzymatically with Cathepsin C under the following reaction conditions. A 50% saturated ammonium sulfate was added to precipitate proteins for a removal of the low molecular substances after enzymatic digestion.

Reaction conditions for cathepsin C

| Composition | |
| --- | --- |
| Substrate: Human glicentin fused protein 1 mg/ml | 5 ml |
| Inhibitor: 25 mM Leupeptin | 0.01 ml |
| Reducing agent: 1 M cystein | 0.06 ml |
| Buffer: 0.5 M NaAco, pH 5.0 0.05 M NaCl | 1.0 ml |
| Enzyme: Bovine cathepsin C 20 Units/ml | 0.025 ml |
| Distilled water: | 3.905 ml |

Reaction

Temperature: 25° C.

Time: 3 hours

Leupeptin and bovine cathepsin C used the products manufactured by Boehringer Mannheim Yamanouchi.

EXAMPLE 7

Purification of Human Glicentin

Figure 8:
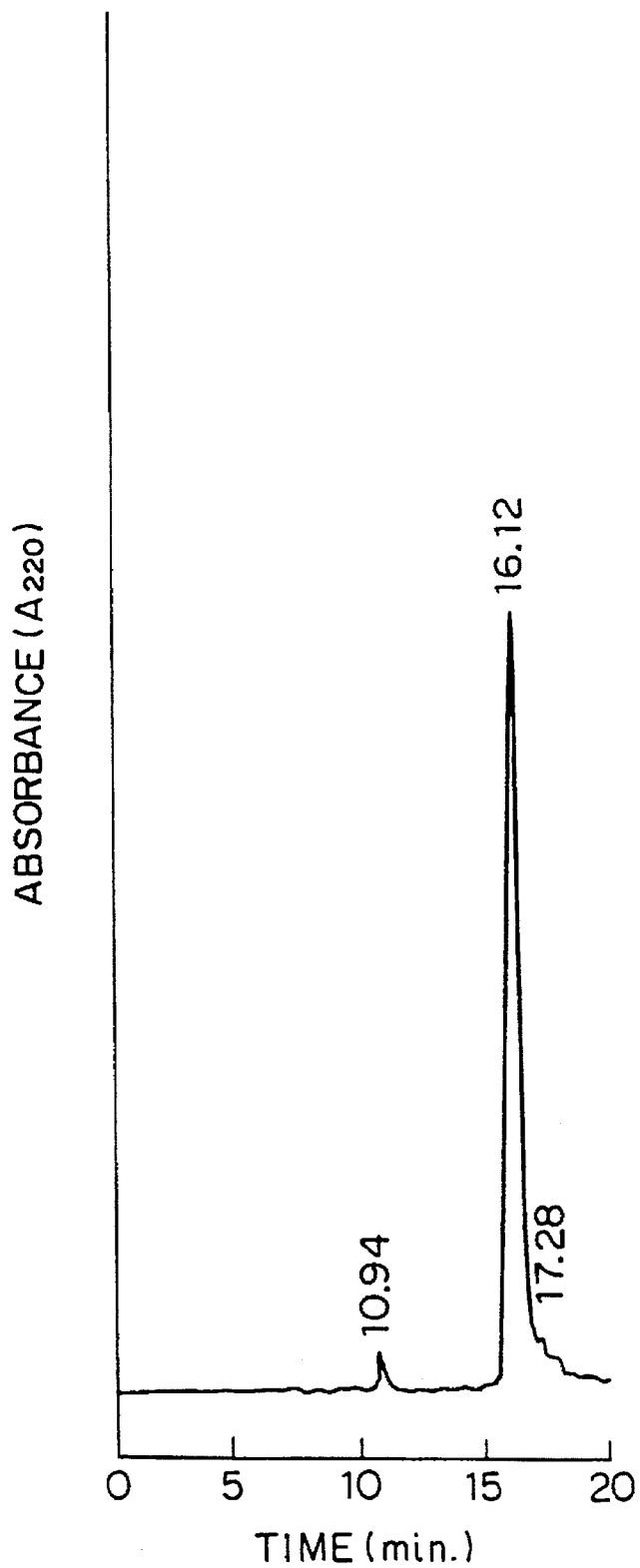
FIG. 8 is a HPLC chromatogram of purified human glicentin in Example 4.
Figure 9:
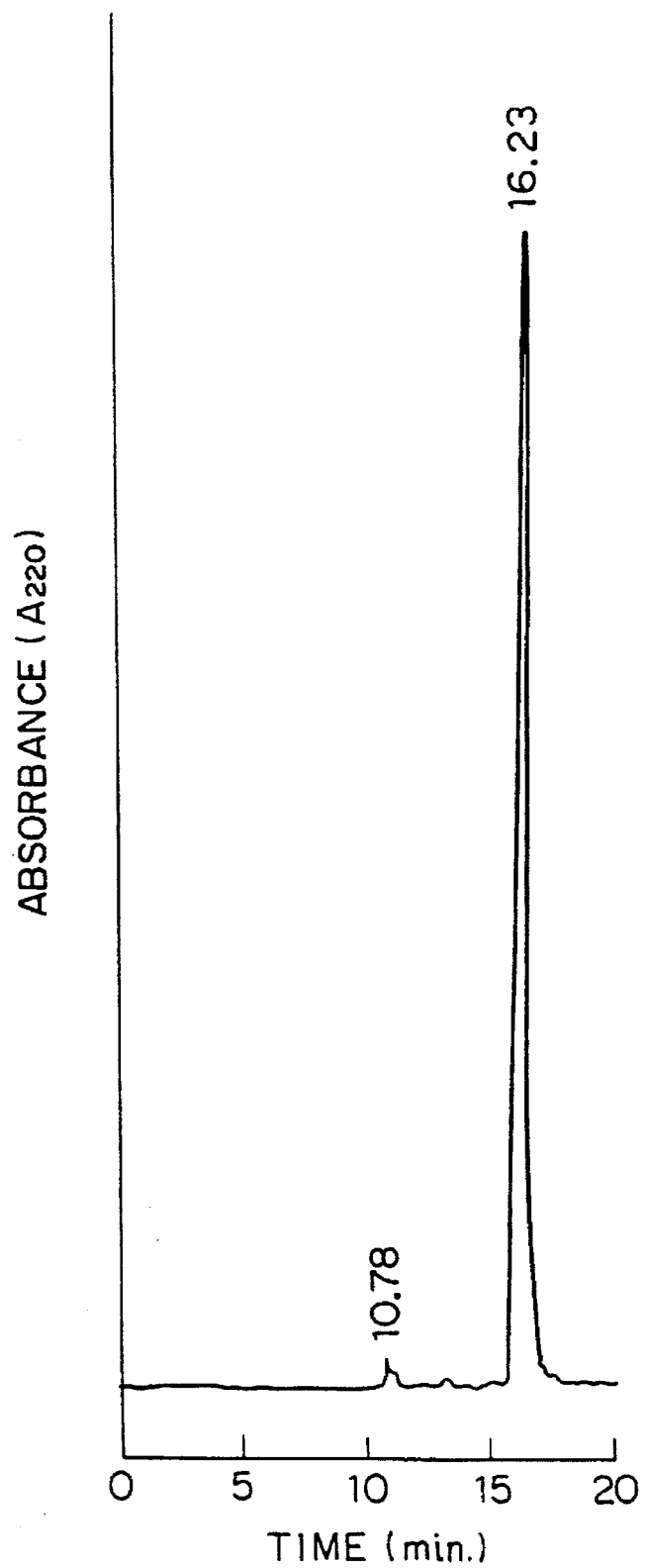
FIG. 9 is a HPLC chromatogram of purified human glicentin in Example 5.

The precipitate shown in Example 6 was dissolved in 50 ml of AES buffer and then added to a thiopropylsepharose 6B column (1 cmφ×3 cm). The passed fractions were combined with the washed fractions, the combined fractions were loaded on a C18 reversed-phase HPLC (the same chromatography conditions as in Example 4), and the fractions of human glicentin were collected to remove contaminant impurities. The fractions of human glicentin were freeze-dried to obtain a pure preparation. An analytical result of the pure preparation by SDS polyacrylamide gel electrophoresis is shown in FIG. 6. The lane 5 is the pure preparation obtained by digesting a fused protein in Example 4. The lane 6 is the pure preparation obtained by digesting a fused protein in Example 5. The chromatograms of the pure preparation by HPLC are shown in FIGS. 8 and 9. The analytical conditions were identical with those shown in Example 4. FIG. 8 shows a chromatogram of a purified product of human glicentin obtained from the fused protein in Example 4. FIG. 9 shows a chromatogram of a purified product of human glicentin obtained from the fused protein in Example 5. Thus, the analyses by both HPLC and electrophoresis indicate that a human glicentin was completely purified.

It was confirmed whether the purified human glicentin retained the amino acid sequence as desired. The human glicentin purified by the process shown in Example 7 was cleaved with lysyl endopeptidase and the 5 peak fragments were collected by a reversed-phase HPLC.

Analysis of the amino acid sequence of each fragment by a peptide sequencer confirmed that the purified human glicentin retained the entire structure of native human glicentin. The methodology of cleavage, distribution and analysis were in accordance with the procedures in the paper edited by Japanese Society of Gut Hormones, 1992, Vol. 11, pp. 394–401.

EXAMPLE 8

Comparison in a cysteine reactivity of the G647-derived human glicentin fused protein and the G662-derived human glicentin fused protein The G647-derived and the G662-derived fused proteins of a human glicentin which were purified by the procedures mentioned in Examples 4 and 5 were respectively adsorbed on 1 ml of thiopropylsepharose 6B until saturation in GAE buffer, by which it was compared how maximum degree of a fused protein in mg can be adsorbed on 1 ml carrier. The adsorbed proteins were respectively eluted in accordance with the procedure described in Example 4 and an amount of a fused protein was calculated from an integrated value by HPLC. The results showed an adsorbance of 4.8 mg/ml gel for the G647-derived fused protein and 11.0 mg/ml for the G662-derived fused protein. It was shown that G662 not containing any basic amino acids before and after a cysteine residue had a higher reactivity to cysteine.

---

What is claimed is:

1. In a process for producing human glicentin, which comprises:

(A) culturing a host which expresses human glicentin, and (B) purifying human glicentin;

wherein the improvement comprises:

(i) culturing a host which expresses a DNA molecule which encodes a fusion protein and which comprises a first segment coding for human glicentin, and a second segment coding for a second peptide and having the amino acid sequence of SEQ ID NO: 14, wherein the N-terminus of human glicentin is fused via a peptide bond to the C-terminus of said second peptide which contains a cysteine residue;

(ii) isolating said fusion protein by forming a covalent bond between a cysteine residue in the second peptide and a thiol group in the stationary phase of a chromatography column or with a thiol-containing reagent, washing said chromatography column, and eluting said fusion peptide from said chromatography column by breaking said covalent bond;

(iii) digesting said fusion protein with cathepsin C to form human glicentin; and (iv) purifying and isolating human glicentin from a mixture of the undigested fusion protein and human glicentin by forming a covalent bond between a cysteine residue in the second peptide and a thiol group in the stationary phase of a chromatography column or with a thiol-containing reagent.

2. In a process for producing human glicentin, which comprises:

(A) culturing a host which expresses human glicentin, and (B) purifying human glicentin;

wherein the improvement comprises:

(i) culturing a host which expresses a DNA molecule which encodes a fusion protein and which comprises a first segment coding for human glicentin, and a second segment coding for a second peptide and having the amino acid sequence of SEQ ID NO: 15, wherein the N-terminus of human glicentin is fused via a peptide bond to the C-terminus of said second peptide which contains a cysteine residue;

(ii) isolating said fusion protein by forming a covalent bond between a cysteine residue in the second peptide and a thiol group in the stationary phase of a chromatography column or with a thiol-containing reagent, washing said chromatography column, and eluting said fusion peptide from said chromatography column by breaking said covalent bond;

(iii) digesting said fusion protein with cathepsin C to form human glicentin; and (iv) purifying and isolating human glicentin from a mixture of the undigested fusion protein and human glicentin by forming a covalent bond between a cysteine residue in the second peptide and a thiol group in the stationary phase of a chromatography column or with a thiol-containing reagent.

3. A fusion protein comprising glicentin linked at its N-terminus via a peptide bond to the C-terminus of a peptide having the amino acid sequence of SEQ ID NO: 14.

4. A fusion protein comprising glicentin linked at its N-terminus via a peptide bond to the C-terminus of a peptide having the amino acid sequence of SEQ ID NO: 15.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA"

( x i ) SEQUENCE DESCRIPTION: SEQ ID NO:1:

GATCCTTAGC GTAGGCCTT            19

( 2 ) INFORMATION FOR SEQ ID NO:2:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA"

( x i ) SEQUENCE DESCRIPTION: SEQ ID NO:2:

GATCAAGGCC TACGCTAAG            19

( 2 ) INFORMATION FOR SEQ ID NO:3:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "SYNTHETIC DNA"

( x i ) SEQUENCE DESCRIPTION: SEQ ID NO:3:

GGATCCTTAG CGTAGGCCT            19

( 2 ) INFORMATION FOR SEQ ID NO:4:

( i ) SEQUENCE CHARACTERISTICS:
        ( A ) LENGTH: 19 base pairs
        ( B ) TYPE: nucleic acid ( C ) STRANDEDNESS: single
( D ) TOPOLOGY: linear ( i i ) MOLECULE TYPE: other nucleic acid
( A ) DESCRIPTION: /desc = "SYNTHETIC DNA"

( x i ) SEQUENCE DESCRIPTION: SEQ ID NO:4:

CATGGCCCGG GACAGCACA 19

( 2 ) INFORMATION FOR SEQ ID NO:5:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "SYNTHETIC DNA"

( x i ) SEQUENCE DESCRIPTION: SEQ ID NO:5:

AGCTTGTGCT GTCCCGGGC 19

( 2 ) INFORMATION FOR SEQ ID NO:6:

( i ) SEQUENCE CHARACTERISTICS:
( A ) LENGTH: 23 base pairs
( B ) TYPE: nucleic acid
( C ) STRANDEDNESS: double
( D ) TOPOLOGY: linear ( i i ) MOLECULE TYPE: other nucleic acid
( A ) DESCRIPTION: /desc = "SYNTHETIC DNA"

( x i ) SEQUENCE DESCRIPTION: SEQ ID NO:6:

CCATGGCCCG GGACAGCAAG CTT 23

( 2 ) INFORMATION FOR SEQ ID NO:7:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "SYNTHETIC DNA"

( x i ) SEQUENCE DESCRIPTION: SEQ ID NO:7:

AATTCAGATC TATCGAAGGT CGACGTTCTC TGCA 34

( 2 ) INFORMATION FOR SEQ ID NO:8:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "SYNTHETIC DNA"

( x i ) SEQUENCE DESCRIPTION: SEQ ID NO:8:

GAGAACGTCG ACCTTCGATA GACTG 25

( 2 ) INFORMATION FOR SEQ ID NO:9:

( i ) SEQUENCE CHARACTERISTICS:
( A ) LENGTH: 36 base pairs
( B ) TYPE: nucleic acid ( C ) STRANDEDNESS: double
( D ) TOPOLOGY: linear ( i i ) MOLECULE TYPE: other nucleic acid
( A ) DESCRIPTION: /desc = "SYNTHETIC DNA"

( x i ) SEQUENCE DESCRIPTION: SEQ ID NO:9:

GAATTCAGAT CTATCGAAGG TCGACGTTCT CTGCAG     36

( 2 ) INFORMATION FOR SEQ ID NO:10:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "SYNTHETIC DNA"

( x i ) SEQUENCE DESCRIPTION: SEQ ID NO:10:

TATGGCTAGC ATGACTGGTG GACAGCAAAT GTGTCGTTCC CTGCA     45

( 2 ) INFORMATION FOR SEQ ID NO:11:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "SYNTHETIC DNA"

( x i ) SEQUENCE DESCRIPTION: SEQ ID NO:11:

GGGAACGACA CATTTGCTGT CCACCAGTCA TGCTAGCCA     39

( 2 ) INFORMATION FOR SEQ ID NO:12:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "SYNTHETIC DNA"

( x i ) SEQUENCE DESCRIPTION: SEQ ID NO:12:

TATGGCTAGC ATGACTGGTC GTCAGCAATG TGGTCGTTCC CTGCA     45

( 2 ) INFORMATION FOR SEQ ID NO:13:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "SYNTHETIC DNA"

( x i ) SEQUENCE DESCRIPTION: SEQ ID NO:13:

GGGAACGACC ACATTGCTGA CGACCAGTCA TGCTAGCCA     39

( 2 ) INFORMATION FOR SEQ ID NO:14:

( i ) SEQUENCE CHARACTERISTICS:
( A ) LENGTH: 10 amino acids
( B ) TYPE: amino acid

```
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

Ala  Ser  Met  Thr  Gly  Arg  Gln  Gln  Cys  Gly
    1                   5                        10

( 2 ) INFORMATION FOR SEQ ID NO:15:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

Ala  Ser  Met  Thr  Gly  Gly  Gln  Gln  Met  Cys
    1                   5                        10
```